(12) United States Patent
Bhattacharyya et al.

(10) Patent No.: US 11,104,622 B2
(45) Date of Patent: Aug. 31, 2021

(54) LIQUID ACID CATALYZED ALKYLATION PROCESS

(71) Applicant: UOP LLC, Des Plaines, IL (US)

(72) Inventors: Alakananda Bhattacharyya, Glen Ellyn, IL (US); Jeffery C. Bricker, Buffalo Grove, IL (US); Mark G. Riley, Hinsdale, IL (US); Andrey O. Kuzmin, Arbuzova (RU)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/734,475

(22) Filed: Jan. 6, 2020

(65) Prior Publication Data

US 2020/0239382 A1    Jul. 30, 2020

(30) Foreign Application Priority Data

Jan. 28, 2019    (RU) ............................ RU2019102207

(51) Int. Cl.
   *C07C 2/70*    (2006.01)
(52) U.S. Cl.
   CPC .......... *C07C 2/70* (2013.01); *C07C 2527/054* (2013.01); *C07C 2527/1206* (2013.01)
(58) Field of Classification Search
   CPC .... C07C 2/70; C07C 9/16; C07C 9/21; C07C 2527/054; C07C 2527/10; C07C 2527/1206; B01J 19/24; B01J 19/26; B01J 2219/00103; B01J 2219/24; B01J 2231/32; B01J 31/128
   See application file for complete search history.

(56) References Cited

U.S. PATENT DOCUMENTS

| | | |
|---|---|---|
| 3,364,280 A | 1/1968 | Kramer |
| 3,870,765 A | 3/1975 | McCoy et al. |
| 3,956,417 A | 5/1976 | Franz et al. |
| 4,041,102 A | 8/1977 | Wronka |
| 4,467,132 A | 8/1984 | Go et al. |
| 4,595,512 A | 6/1986 | Tellier et al. |
| 4,795,728 A | 1/1989 | Kocal |
| 4,891,466 A | 1/1990 | Kocal |
| 2019/0001314 A1* | 1/2019 | Buchbinder ......... B01J 31/0288 |

FOREIGN PATENT DOCUMENTS

| | | |
|---|---|---|
| EP | 139504 A1 | 7/1983 |
| EP | 274805 A1 | 7/1988 |
| SU | 988328 A1 | 1/1983 |

OTHER PUBLICATIONS

Meng, Xiangzhan, Carbon-Based Materials Enhanced Emulsification to Improve Product Distribution in Isobutane/Butene Alkylation Catalyzed by Sulfuric Acid, Ind. Eng. Chem. Res. 2017, 56, 7700,7707.

(Continued)

*Primary Examiner* — Sharon Pregler

(57) ABSTRACT

A process for acid catalyzed alkylation involving the use of surfactants which form bi-continuous micro-emulsions with the liquid acid and the hydrocarbon is described. The bicontinuous phase formed between the hydrocarbon and liquid acid phases at surfactant addition facilitates and improves the liquid acid catalyzed alkylation reactions including motor-fuel alkylation reaction.

20 Claims, 1 Drawing Sheet

(56) References Cited

OTHER PUBLICATIONS

Krylov, V.A., Sulfuric Acid Alkylation in the Presence of Surfactants, 1990 Plenum Publishing Corporation, Translated from Khimiya i Tekhnologiya Topliv i Masel, No. 1, pp. 19-21, Jan. 1990.

Salager, J.L., The fundamental basis for the action of a chemical dehydrant. Influence of the physical and chemical formulation on the stability of an emulsion, International Chemical Engineering, 1990, 30, 103-106.

Branzaru, Jeannie, Introduction to Sulfuric Acid Alkylation Unit Process Design, Stratco, Inc., Nov. 2001.

Chen, Wen-Shing, Solubility measurements of isobutane/alkenes in sulfuric acid and applications to alkylation, Applied Catalysis, A: General (2003), 255(2), 231-237.

Chen, Wen-Shing, Studies on the Sulfuric Acid Catalyzed Isopentane/Olefins Alkylation, Journal of Petroleum, Sep. 2000, vol. 36, No. 3.

Cosgrove, Terence, Chapter 3: Microemulsions, published in Colloid Science: Principles, Methods and Applications, Aug. 30, 2005.

\* cited by examiner

LIQUID ACID CATALYZED ALKYLATION PROCESS

RELATED APPLICATIONS

This application claims the benefit of Russian Application Ser. No. 2019102207 filed on Jan. 28, 2019, the entirety of which is incorporated herein by reference.

BACKGROUND

Alkylation is typically used to combine light olefins, for example mixtures of alkenes such as propylene and butylene, with isobutane to produce a relatively high-octane branched-chain paraffinic hydrocarbon fuel, including iso-heptane and isooctane. Similarly, an alkylation reaction can be performed using an aromatic compound such as benzene in place of the isobutane. When using benzene, the product resulting from the alkylation reaction is an alkylbenzene (e.g. ethylbenzene, cumene, dodecylbenzene, etc.).

The alkylation of paraffins with olefins for the production of alkylate for gasoline can use a variety of catalysts. The choice of catalyst depends on the end product a producer desires. Typical alkylation catalysts include concentrated sulfuric acid or hydrofluoric acid. However, the use of sulfuric acid and hydrofluoric acid in industrial processes requires a variety of environmental controls because they are hazardous and corrosive.

Solid catalysts are also used for alkylation. However, solid catalysts are generally rapidly deactivated by the presence of water, which may be present in the feed.

Acidic ionic liquids can be used as an alternative to the commonly used strong acid catalysts in alkylation processes. Ionic liquids are salts comprised of cations and anions which typically melt below about 100° C. Ionic liquids are essentially salts in a liquid state, and are described in U.S. Pat. Nos. 4,764,440, 5,104,840, and 5,824,832. The properties vary extensively for different ionic liquids, and the use of ionic liquids depends on the properties of a given ionic liquid. Depending on the organic cation of the ionic liquid and the anion, the ionic liquid can have very different properties.

The alkylation reaction rate is limited by the low solubility of isoalkanes in sulfuric acid, and rigorous agitation is required to create a large interfacial area to allow for sufficient mass transfer. Surfactants are well known to aid mass transfer between the phases by the creation of micelles and are the subject of numerous patents in the 1940s, 1950's, and 1960s.

However, with most surfactants, some of the surfactant is soluble in the hydrocarbon phase and this causes problems during alkaline water washing of the alkylate. The surfactant makes it harder to separate the alkylate (oil) from the liquid acid. Surfactant carry-over causes problems in other sections of the alkylation complex. As a consequence, surfactants do not appear to be used commercially.

Therefore, there is a need for an improved alkylation process.

SUMMARY AND DETAILED DESCRIPTION

It has been discovered that surfactants which form bi-continuous micro-emulsions with the liquid acid and the hydrocarbons, such as dioctadecyl-dimethyl-ammonium chloride (DODMAC) can be used in a motor fuel alkylation process. The use of microheterogeneous Winsor Type III phase systems, which contain a zero-curvature bicontinuous nano-structured phase formed between oil and polar phases at surfactant addition, as a medium for "micellar catalysis" for facilitating and improvement of liquid acid catalyzed motor-fuel alkylation reaction.

A Winsor Type III micro-emulsion system is a three-phase system where a surfactant-rich middle phase co-exists with both the polar phase and oil surfactant-poor phases. The Winsor R ratio compares the tendency for an amphiphile to disperse into oil to its tendency to dissolve in water. The Winsor R ratio of cohesive energies stemming from interaction of the interfacial layer with oil divided by energies resulting from interactions with water determines the preferred interfacial curvature. A balanced interfacial layer is represented by Winsor R=1.

Figure 1A:
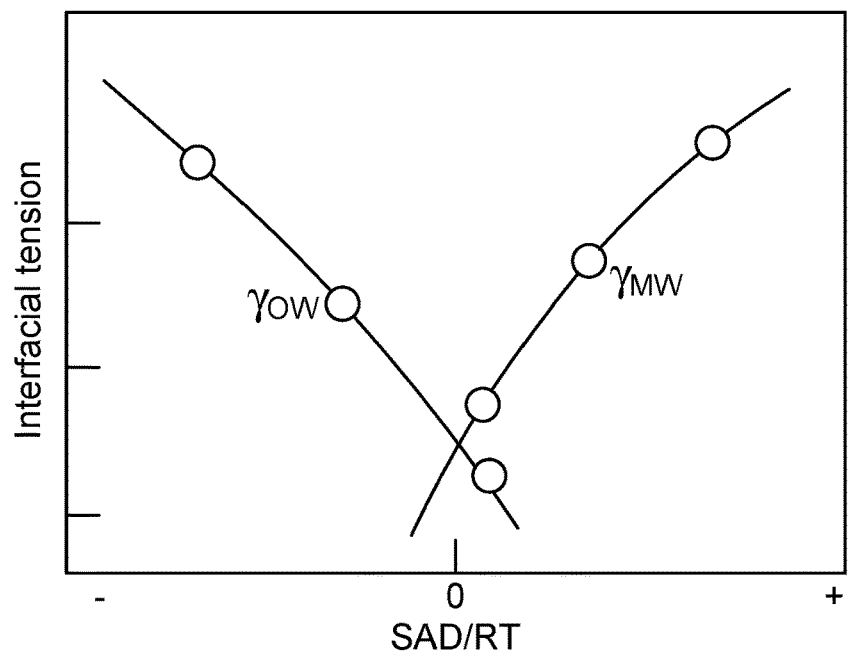
FIGS. 1A-C show the interfacial tension, the solubilization parameters, and phase behavior of a system.
Figure 1B:
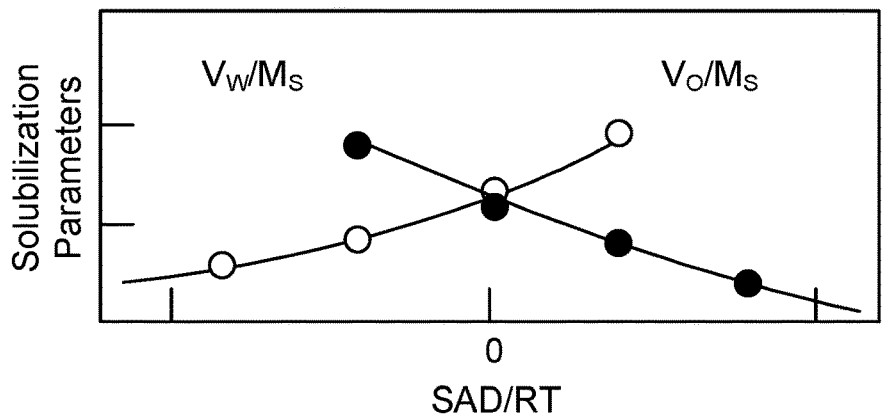
Figure 1C:
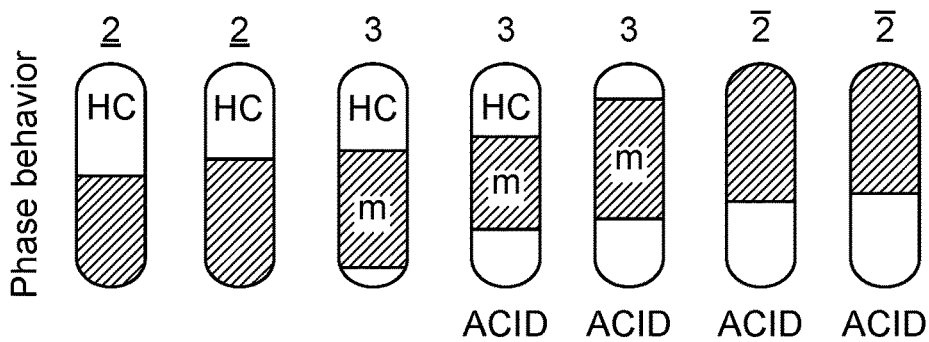

Surfactant affinity difference (SAD) is a surfactant property in a polar/non-polar two-phase system which is responsible for how the system behaves on the addition of the surfactant. A value close to SAD/RT=0 typically means the formation of the third phase discussed above. SAD/RT can be measured as described in Salager, "The fundamental basis for the action of a chemical dehydrant. Influence of the physical and chemical formulation on the stability of an emulsion," Int'l Chem. Eng., 1990, 30, p. 103-116, which is incorporated herein by reference in its entirety. The type of emulsion can be determined in different ways. For example, the electrical conductivity can be measured. The electrical conductivity is roughly proportional to the conductivity of the external phase and the volume percent of the external phase in the emulsion. Another method involves measuring the interfacial tension. FIGS. 1A-C show the interfacial tension, the solubilization parameters, and phase behavior of a system.

Suitable surfactants have a solubility at 25° C. of 0.5 wt. % or less in the olefin, the isoparaffin, the liquid acid catalyst, and the alkylation product, or 0.4 wt % or less, or 0.3 wt % or less, or 0.2 wt % or less, or 0.1 wt % or less, or 0.09 wt % or less, or 0.08 wt % or less, or 0.07 wt % or less, or 0.06 wt % or less, or 0.05 wt % or less. The ultra-low solubility helps to reduce the amount of surfactant and liquid acid in the alkylation product after separation.

Alkylation processes incorporating surfactants which form a microheterogeneous Winsor Type III phase system have shown one or more of: reduced liquid acid consumption, lower acid circulation and inventory, increased reaction rate, and improved alkylate selectivity and yield.

One aspect of the invention is a process for acid catalyzed alkylation. In one embodiment, the process comprises reacting an olefin and an isoparaffin or an aromatic compound in the presence of a liquid acid catalyst and a surfactant in an alkylation reaction zone operating at alkylation reaction conditions to form a reaction mixture comprising an alkylation product and the alkylation catalyst, wherein the surfactant has a solubility at 25° C. of 0.5% or less in the olefin, the isoparaffin, the liquid acid catalyst, and the alkylation product. The reaction mixture comprises a Winsor Type III phase system.

In some embodiments, the surfactant comprises a quaternary ammonium cationic salt, or a quaternary phosphonium cationic salt, or combinations thereof.

In some embodiments, the quaternary ammonium cationic salt comprises a quaternary ammonium halide, a quaternary ammonium sulfate, a quaternary ammonium hydrogen sulfate, a quaternary ammonium nitrate, a quaternary ammonium carbonate, a quaternary ammonium bicarbonate, a quaternary phosphonium halide, a quaternary phosphonium sulfate, a quaternary phosphonium hydrogen sulfate, a quaternary phosphonium nitrate, a quaternary phosphonium carbonate, a quaternary phosphonium bicarbonate, or combinations thereof.

In some embodiments, the surfactant comprises dibutyl dioctyldecyl ammonium chloride, dimethyl dipentadecyl ammonium chloride, diethyl dipentadecyl ammonium chloride, dipropyl dipentadecyl ammonium chloride, dibutyl dipentadecyl ammonium chloride, dimethyl dihexadecyl ammonium chloride, diethyl dihexadecyl ammonium chloride, dipropyl dihexadecyl ammonium chloride, dibutyl dihexadecyl ammonium chloride, dimethyl dioctadecyl ammonium chloride, diethyl dioctadecyl ammonium chloride, dipropyl dioctadecyl ammonium chloride, dimethyl dinonadecyl ammonium chloride, diethyl dinonadecyl ammonium chloride, dipropyl dinonadecyl ammonium chloride, dibutyl dinonadecyl ammonium chloride, dimethyl diicosylecyl ammonium chloride, diethyl diicosyldecyl ammonium chloride, dipropyl diicosyldecyl ammonium chloride, dibutyl diicosyldecyl ammonium chloride, or combinations thereof. Similar sulfates, hydrogen sulfates, nitrates, carbonates, bicarbonates, other halides, or combinations thereof could be used.

In some embodiments, the surfactant comprises fat carbonic acid or corresponding salt, or organosulfate salts like sodium dodecyl sulfate, or alkyl phosphates.

In some embodiments, the process further comprises separating the alkylation product from the reaction mixture.

In some embodiments, the amount of the surfactant is in a range of 0.010 to 0.25 wt % of an amount of the liquid acid.

In some embodiments, the process further comprises an additional surfactant or co-surfactant.

In some embodiments, a second surfactant or co-surfactants may be fat carbonic acids, organosulfate salts like sodium dodecyl sulfate as anionic surfactants, alkyl phosphates as non-ionic surfactants and so on.

All surfactants must be stable under reaction conditions.

In some embodiments, a molar feed ratio of liquid acid to olefin is in a range of 0.005:1 to 100:1.

In some embodiments, the process further comprises recycling at least a portion of the liquid acid, the surfactant, or both.

In some embodiments, the liquid acid comprises sulfuric acid, hydrofluoric acid, an acidic ionic liquid, or combinations thereof.

In some embodiments, the olefin comprises a $C_2$-$C_{20}$ olefin.

In some embodiments, the alkylation reaction conditions include at least one of: a temperature of from 0° to 50° C., a pressure of from 100 kPa to 2100 kPa, and a liquid hourly space velocity of from 2.0 to 60.0 $hr^{-1}$.

In some embodiments, the process further comprises at least one of: sensing at least one parameter of the process and generating a signal or data from the sensing; or generating and transmitting a signal; or generating and transmitting data.

Another aspect of the invention is a process for sulfuric acid catalyzed alkylation. In one embodiment, the process comprises reacting an olefin and an isoparaffin or aromatic compound in the presence of a sulfuric acid catalyst and a surfactant in an alkylation reaction zone operating at alkylation reaction conditions to form a reaction mixture comprising an alkylation product, and the sulfuric acid, wherein the surfactant has a solubility at room temperature of 0.5% or less in the olefin, the isoparaffin or aromatic compound, the sulfuric acid, and the alkylation product, wherein an amount of the surfactant is in a range of 0.010 to 0.25 wt % of an amount of the sulfuric acid, and wherein a molar feed ratio of liquid acid to olefin is in a range of 0.005 to 100.

In some embodiments, the surfactant comprises a quaternary ammonium cationic salt. In some embodiments, the surfactant comprises dibutyl dioctyldecyl ammonium chloride, dimethyl dipentadecyl ammonium chloride, diethyl dipentadecyl ammonium chloride, dipropyl dipentadecyl ammonium chloride, dibutyl dipentadecyl ammonium chloride, dimethyl dihexadecyl ammonium chloride, diethyl dihexadecyl ammonium chloride, dipropyl dihexadecyl ammonium chloride, dibutyl dihexadecyl ammonium chloride, dimethyl dioctadecyl ammonium chloride, diethyl dioctadecyl ammonium chloride, dipropyl dioctadecyl ammonium chloride, dimethyl dinonadecyl ammonium chloride, diethyl dinonadecyl ammonium chloride, dipropyl dinonadecyl ammonium chloride, dibutyl dinonadecyl ammonium chloride, dimethyl diicosylecyl ammonium chloride, diethyl diicosyldecyl ammonium chloride, dipropyl diicosyldecyl ammonium chloride, dibutyl diicosyldecyl ammonium chloride, or combinations thereof.

In some embodiments, the process further comprises separating the alkylation product from the reaction mixture.

In some embodiments, the process further comprises recycling at least a portion of the sulfuric acid, the surfactant, or both.

In some embodiments, the olefin comprises a $C_2$-$C_{20}$ olefin.

In some embodiments, the alkylation reaction conditions include one or more of: a temperature of from 0° to 50° C., a pressure of from 100 kPa to 2100 kPa, and a liquid hourly space velocity of from 2.0 to 60.0 $hr^{-1}$.

The surfactant can be added to the liquid acid catalyst, and the liquid acid catalyst/surfactant mixture can be mixed with the isoparaffin or aromatic compound, following by mixing with the olefin. When utilizing this process in an existing plant, the point of addition of the surfactant will likely depend on the reactor system layout.

The process involves reacting an olefin and an isoparaffin or an aromatic compound in the presence of a liquid acid catalyst and a surfactant in an alkylation reaction zone to form an alkylate. The reaction mixture comprises alkylation product (alkylate), any unreacted olefin and/or isoparaffin, as well as the liquid acid catalyst.

Typical paraffins include isobutane and higher homologues having a tertiary carbon atom, such as 2-methylbutane and 2,4-dimethylpentane. Other alkylatable materials include benzene, toluene, xylene, naphthenes, phenols, cresols, aromatic amines, thiophenes, and isoparaffinic mercaptans.

Olefins also comprise a feed component to the process. Suitable olefins are typically straight or branched hydrocarbons containing one or more carbon-carbon double bond. In some embodiments, the olefin contains from 2 to 20 carbon atoms, or 2 to 12, or 2 to 11, or 2 to 8, or 3 to 20 carbon atoms, or 3 to 12, or 3 to 11, or 3 to 8. In some embodiments, the olefin contains from 3 to 5 carbon atoms. In some embodiments, the olefin contains from 5 to 16 carbon atoms.

The alkylation reaction is promoted through the presence of a liquid acid catalyst, including mineral acids, such as hydrofluoric acid, sulfuric acid, phosphoric acid, and the like, as well as acidic ionic liquids, or mixtures thereof. The mineral acids are maintained in a liquid phase containing a minimum of water to reduce corrosion problems. The liquid acid may also comprise a mixture of mineral acid or ionic liquid with a metal halide such as aluminum chloride, aluminum bromide, boron trifluoride, and other proton donors. Any liquid acid catalyst known in the prior art can be used. In some embodiments, the liquid acid catalyst is sulfuric acid.

Another component is the surfactant. The surfactant has a solubility at 25° C. of 0.5 wt. % or less in the olefin, the isoparaffin, the liquid acid catalyst, and the alkylation product, or 0.4 wt % or less, or 0.3 wt % or less, or 0.2 wt % or less, or 0.1 wt % or less, or 0.09% or less, or 0.08% or less, or 0.07% or less, or 0.06% or less, or 0.05% or less.

The amount of the surfactant is in the range of 0.001 to 0.25 wt % of the amount of the liquid acid, or 0.010 to 0.20 wt %, or 0.010 to 0.15 wt %, or 0.010 to 0.10 wt %, or 0.010 to 0.090 wt %, or 0.010 to 0.080 wt %, or 0.010 to 0.070 wt %, or 0.010 to 0.060 wt %, or 0.010 to 0.050 wt %.

Any surfactant meeting the criteria for forming a Winsor Type III phase can be used. Suitable surfactants, include, but are not limited to, quaternary ammonium cationic salts, or quaternary ammonium cationic salts, or combinations thereof. Suitable quaternary ammonium salts include, but are not limited to, quaternary ammonium halides, a quaternary ammonium sulfates, quaternary ammonium hydrogen sulfates, quaternary ammonium nitrates, quaternary ammonium carbonates, quaternary ammonium bicarbonates, quaternary phosphonium halides, quaternary phosphonium sulfates, quaternary phosphonium hydrogen sulfates, quaternary phosphonium nitrates, quaternary phosphonium carbonates, quaternary phosphonium bicarbonates, or combinations thereof. Suitable surfactants include, but are not limited to, dibutyl dioctyldecyl ammonium chloride, dimethyl dipentadecyl ammonium chloride, diethyl dipentadecyl ammonium chloride, dipropyl dipentadecyl ammonium chloride, dibutyl dipentadecyl ammonium chloride, dimethyl dihexadecyl ammonium chloride, diethyl dihexadecyl ammonium chloride, dipropyl dihexadecyl ammonium chloride, dibutyl dihexadecyl ammonium chloride, dimethyl dioctadecyl ammonium chloride, diethyl dioctadecyl ammonium chloride, dipropyl dioctadecyl ammonium chloride, dimethyl dinonadecyl ammonium chloride, diethyl dinonadecyl ammonium chloride, dipropyl dinonadecyl ammonium chloride, dibutyl dinonadecyl ammonium chloride, dimethyl diicosylecyl ammonium chloride, diethyl diicosyldecyl ammonium chloride, dipropyl diicosyldecyl ammonium chloride, dibutyl diicosyldecyl ammonium chloride, or combinations thereof.

The process may also comprise one or more additional surfactants or co-surfactants. They may have different solubility from main surfactant but not greater than 0.5 wt. % in the olefin, the isoparaffin, and/or the alkylation product. The additional surfactant can be present in an amount so that the total amount of surfactant and additional surfactants/co-surfactants is in the range of 0.001 to 3 wt %. Suitable additional or co-surfactants include, but are not limited to, fatty carboxylic acids (fatty acids) or corresponding salts, organosulfate salts like sodium dodecyl sulfate, or alkyl phosphates The process involves the acid-catalyzed alkylation of an isoparaffin or aromatic compound with an olefin in an alkylation reactor to (produce high octane alkylate. The alkylation conditions include a pressure sufficient to maintain the hydrocarbons and acid in a liquid phase, with a general range being from about 100 kPa to 4100 kPa (1 to 40 atmospheres). The alkylation reaction may take place at temperatures of from 0° C. to 390° C., or 0° C. to 275° C. The reaction also occurs at liquid hourly space velocities ranging from 0.1 to 100 hr$^{-1}$, or 0.5 to 60 hr$^{-1}$. In some embodiments, the conditions include a temperature of from 0° to 50° C., a pressure of from 100 kPa to 2100 kPa, and a liquid hourly space velocity of from 2.0 to 60.0 hr$^{-1}$.

One variable in the alkylation reaction process is the molar ratio of the isoparaffin or aromatic compound to the olefin. As known to those skilled in the art, typical alkylation zone conditions necessarily include a high ratio of the molar concentration of the isoparaffin or aromatic compound to the molar concentration of the olefin in order to produce a high quality alkylate product. A broad range of this ratio is from about 2:1 to 20:1. For the isobutane/butane system, the isoparaffin:olefin ratio is typically in the range of 5:1 to 10:1, for example.

Another variable in the process is the molar ratio of the liquid acid catalyst to the olefin or aromatic compound being fed to the alkylation reaction zone. This ratio should be minimized. A low molar ratio of acid catalyst to olefin means less acid catalyst is required in the process. It also means that a smaller supply of liquid acid is needed to maintain acid inventory. By minimizing this ratio, the volume of liquid acid catalyst necessary is minimized resulting in a reduction in the potential environmental and safety dangers posed by the liquid acid catalyst. The liquid acid to olefin molar feed ratio may vary from 0.005:1 to 100:1, or 0.005:1 to 80:1, or 0.005:1 to 60:1, or 0.005:1 to 40:1, or 0.005:1 to 30:1, or 0.005:1 to 25:1, or 0.005:1 to 20:1, or 0.005:1 to 10:1, or 0.01:1 to 100:1, or 0.01:1 to 80:1, or 0.01:1 to 60:1, or 0.01:1 to 40:1, or 0.01:1 to 30:1, or 0.01:1 to 25:1, or 0.01:1 to 20:1, or 0.01:1 to 10:1, or 0.1:1 to 100:1, or 0.1:1 to 80:1, or 0.1:1 to 60:1, or 0.1:1 to 40:1, or 0.1:1 to 30:1, or 0.1:1 to 25:1, or 0.1:1 to 20:1, or 0.1:1 to 10:1, or 1:1 to 100:1, or 1:1 to 80:1, or 1:1 to 60:1, or 1:1 to 40:1, or 1:1 to 30:1, or 1:1 to 25:1, or 1:1 to 20:1, or 1:1 to 10:1.

In some embodiments, the feedstock should comprise a $C_3$ to $C_5$ olefin, an isoparaffin, and sulfuric acid. Reaction zone conditions for the production of a motor fuel alkylate from these feed components can include a temperature of from 0° C. to 50° C., a pressure of from 100 to 2100 kPa, and a liquid hourly space velocity of from 2 to 60 hr$^{-1}$. The sulfuric acid to $C_3$-$C_5$ olefin volume feed ratio can be in the range from 100:1 to 1:200, or 100:1 to 1:150, or 100:1 to 1:100, or 100:1 to 1:75, or 100:1 to 1:50, or 80:1 to 1:200, or 80:1 to 1:150, or 80:1 to 1:100, or 80:1 to 1:75, or 80:1 to 1:50, or 60:1 to 1:200, or 60:1 to 1:150, or 60:1 to 1:100, or 60:1 to 1:75, or 60:1 to 1:50, or 50:1 to 1:200, or 50:1 to 1:150, or 50:1 to 1:100, or 50:1 to 1:75, or 50:1 to 1:50, or 40:1 to 1:200, or 40:1 to 1:150, or 40:1 to 1:100, or 40:1 to 1:75, or 40:1 to 1:50, or 30:1 to 1:200, or 30:1 to 1:150, or 30:1 to 1:100, or 30:1 to 1:75, or 30:1 to 1:50, or 20:1 to 1:200, or 20:1 to 1:150, or 20:1 to 1:100, or 20:1 to 1:75, or 20:1 to 1:50

EXAMPLES

Experiments were conducted to demonstrate and evaluate the invention.

A stirred stainless steel lab reactor (100 ml volume) with pitched blade turbine operated in batch mode was used to carry out alkylation experiments. The reactor was cooled during the experiments with the help of a refrigerated circulator.

If surfactant was used in an experiment, it was initially dissolved in $H_2SO_4$ with help of heating (~50° C.) followed by solution cooling. The reactor for alkylation was purged with dry nitrogen and cooled. Sulfuric acid (SA) (with or without surfactant) was loaded into the reactor with help of a pump, followed by either isopentane (iP) or liquid isosobutane (iB) pumping. The reactor was cold and kept stirred for approximately a half an hour and then gaseous 1-butene (1b) started to be added. At each stage, the reactor weight was measured to control all introduced reactants amounts. After reaction completion and waiting for phase separation, a sample of the separated alkylate was taken for GC analysis.

All test experiments were carried out during sufficient time to obtain 100% conversion of olefin which was controlled by GC analysis, at a stirring velocity of 750 rpm, a volume of SA per volume of isoalkane ratio of 1:1, a T=6÷7° C. A typical space velocity (SV) of olefin addition was SV of 0.3 h$^{-1}$, the isoalkane/olefin total ratio iA/O=7, if different values are not given in the specific example.

Example 1

Into a two-phase system comprising of two immiscible liquids, 10 ml of concentrated 96 wt. % sulfuric acid (SA) and 10 ml of isopentane (iP), 184 mg (~1 wt. % of an amount of the SA) of DODMAC (dioctadecyl-dimethyl-ammonium chloride) was added, and system was mixed until all the added DODMAC was dissolved at the interface of SA/iP. The solubility of DODMAC in either pure phase was measured with the NMR method as less than 0.04 mg per 100 ml at 25° C. After several days, the emulsified system was completely separated with the formation of approximately 4 ml of a transparent microemulsion phase situated in the middle with approximately equal volumes of SA and iP involved in this middle phase. This system represents a typical Winsor Type III phase system at optimum formulation.

Example 2

Into a two-phase system comprising of two immiscible liquids 10 ml of concentrated 96 wt. % sulfuric acid (SA) and 10 ml of isooctane (iO), 184 mg (~1 wt. % of an amount of the SA) of DODMAC (dioctadecyl-dimethyl-ammonium chloride) was added, and system was mixed until all the added DODMAC was dissolved at the interface of SA/iO. After several days, the emulsified system was completely separated with the formation of two phases with the top one being a pure isooctane phase and the bottom one being a microemulsion containing small quantity of iO dispersed in SA (Winsor Type I system). So, increasing of alkane carbon number (ACN) changed the phase diagram from Winsor Type III to Type I phase diagram.

Example 3

Pure SA catalyzed alkylation reaction of iP and 1-butene (1b) was carried out for comparison. The selectivity of 1b conversion to trimethylhexanes was 26 mol. %, and the selectivity to C9 product was 31 mol. % or 0.71 (C9 mass)/(1b mass). The yield of true alkylate (pure alkylate, e.g., all $C_3$ to $C_5$ components are completely removed) was 1.93 (alkylate mass/1b mass), and the calculated RON number near 84.

Example 4

Pure SA alkylation reaction of iB and 1b was carried out for comparison. The space velocity (SV) of olefin addition was SV=0.5 h$^{-1}$, the isoalkane/olefin total ratio was iA/O=9. The selectivity of 1b conversion to trimethylpentanes was 31 mol. %, and the selectivity to C8 product was 45 mol. % or 0.89 (C8 mass)/(1b mass). The yield of true alkylate was 1.77 (alkylate mass/1b mass). RON number was estimated as 93.

Example 5

As an example, artificially aged SA was used to model a real industrial process as well. To do this, the same sample of SA was used repeatedly to accumulate acid soluble oil (ASO) or conjugated polymers (CP) formed as side products during the alkylation reaction of iP and 1b. The best results in a series of experiments were used. The data are in good accordance with previously published elsewhere (U.S. Pat. No. 5,583,275).

The selectivity of 1b conversion to trimethylhexanes was 70 mol. %, and the selectivity to C9 product was 81 mol. % or 1.85 (C9 mass)/(1b mass). The yield of true alkylate was 3.03 (alkylate mass/1b mass), and the calculated RON number was 87-88.

Example 6

DODMAC modified pure SA catalyzed alkylation reaction of iP and 1b was studied at a surfactant concentration of 0.015 wt. % of the amount of the SA. The selectivity of 1b conversion to trimethylhexanes was 78 mol. %, and the selectivity to C9 product 95 mol. % or 2.2 (C9 mass)/(1b mass). The yield of true alkylate was 3.2 (alkylate mass/1b mass), and the calculated RON number was near 92. The ratio of iP reacted to 1b was near 2 mol/mol, which means that the auto-alkylation route is sufficient due to the excellent availability of iP for reaction. The reaction yield/selectivity was not improved by increasing the DMDOAC concentration above 0.015 wt. %. Increasing temperature had little effect on reaction yield/selectivity up to 17° C.

1H NMR analysis indicated that the amount of acid soluble oils (ASO) formed in SA phase was 10 to 20 times less than that in case of non-modified pure SA catalyzed alkylation process.

Example 7

DODMAC modified pure SA catalyzed alkylation reaction of iB and 1b was studied at a surfactant concentration of 0.025 wt. % of the amount of the SA. The space velocity (SV) of olefin addition was SV=0.5 h$^{-1}$, and the isoalkane/olefin total ratio was iA/O=9. The selectivity of 1b conversion to trimethylpentanes was 88 mol. %, and the selectivity to C8 product was 98 mol. % or 1.96 (C8 mass)/(1b mass). The yield of true alkylate was 2.2 (alkylate mass/1b mass), and the calculated RON number near 100.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for acid catalyzed alkylation comprising reacting an olefin and an isoparaffin or an aromatic compound in the presence of a liquid acid catalyst and a surfactant in an alkylation reaction zone operating at alkylation reaction conditions to form a reaction mixture comprising an alkylation product, wherein the surfactant has a solubility at 25° C. of 0.5% or less in the olefin, the isoparaffin, the liquid acid catalyst, and the alkylation product. An embodiment of the invention is one, any or all of prior embodiments in this paragraph up through the first embodiment in this paragraph wherein the reaction mixture comprises a Winsor Type III phase system. An embodiment of the invention is one, any or all of prior embodiments in this paragraph up through the first embodiment in this paragraph wherein the surfactant comprises a quaternary ammonium cationic salt, or a quaternary phosphonium cationic salt, or combinations thereof. An embodiment of the invention is one, any or all of prior embodiments in this paragraph up through the first embodiment in this paragraph wherein the quaternary ammonium cationic salt or a quaternary phosphonium cationic salt comprises a quaternary ammonium halide, a quaternary ammonium sulfate, a quaternary ammonium hydrogen sulfate, a quaternary ammonium nitrate, a quaternary ammonium carbonate, a quaternary ammonium bicarbonate, a quaternary phosphonium halide, a quaternary phosphonium sulfate, a quaternary phosphonium hydrogen sulfate, a quaternary phosphonium nitrate, a quaternary phosphonium carbonate, a quaternary phosphonium bicarbonate, or combinations thereof. An embodiment of the invention is one, any or all of prior embodiments in this paragraph up through the first embodiment in this paragraph wherein the surfactant comprises dibutyl dioctyldecyl ammonium chloride, dimethyl dipentadecyl ammonium chloride, diethyl dipentadecyl ammonium chloride, dipropyl dipentadecyl ammonium chloride, dibutyl dipentadecyl ammonium chloride, dimethyl dihexadecyl ammonium chloride, diethyl dihexadecyl ammonium chloride, dipropyl dihexadecyl ammonium chloride, dibutyl dihexadecyl ammonium chloride, dimethyl dioctadecyl ammonium chloride, diethyl dioctadecyl ammonium chloride, dipropyl dioctadecyl ammonium chloride, dimethyl dinonadecyl ammonium chloride, diethyl dinonadecyl ammonium chloride, dipropyl dinonadecyl ammonium chloride, dibutyl dinonadecyl ammonium chloride, dimethyl diicosylecyl ammonium chloride, diethyl diicosyldecyl ammonium chloride, dipropyl diicosyldecyl ammonium chloride, dibutyl diicosyldecyl ammonium chloride, or combinations thereof. An embodiment of the invention is one, any or all of prior embodiments in this paragraph up through the first embodiment in this paragraph further comprising separating the alkylation product from the reaction mixture. An embodiment of the invention is one, any or all of prior embodiments in this paragraph up through the first embodiment in this paragraph wherein an amount of the surfactant is in a range of 0.010 to 0.25 wt % of an amount of the liquid acid. An embodiment of the invention is one, any or all of prior embodiments in this paragraph up through the first embodiment in this paragraph further comprising an additional surfactant or co-surfactant. An embodiment of the invention is one, any or all of prior embodiments in this paragraph up through the first embodiment in this paragraph wherein a molar feed ratio of liquid acid to olefin is in a range of 0.0051 to 1001. An embodiment of the invention is one, any or all of prior embodiments in this paragraph up through the first embodiment in this paragraph further comprising recycling at least a portion of the liquid acid, the surfactants, or both. An embodiment of the invention is one, any or all of prior embodiments in this paragraph up through the first embodiment in this paragraph wherein the liquid acid comprises sulfuric acid, hydrofluoric acid, an acidic ionic liquid, or combinations thereof. An embodiment of the invention is one, any or all of prior embodiments in this paragraph up through the first embodiment in this paragraph wherein the olefin comprises a $C_2$-$C_{20}$ olefin. An embodiment of the invention is one, any or all of prior embodiments in this paragraph up through the first embodiment in this paragraph wherein the alkylation reaction conditions include at least one of a temperature of from 0° to 50° C., a pressure of from 100 kPa to 2100 kPa, or a liquid hourly space velocity of from 2.0 to 60.0 $hr^{-1}$. An embodiment of the invention is one, any or all of prior embodiments in this paragraph up through the first embodiment in this paragraph further comprising at least one of sensing at least one parameter of the process and generating a signal or data from the sensing; or generating and transmitting a signal; or generating and transmitting data.

A second embodiment of the invention is a process for sulfuric acid catalyzed alkylation comprising reacting an olefin and an isoparaffin or aromatic compound in the presence of a sulfuric acid catalyst and a surfactant in an alkylation reaction zone operating at alkylation reaction conditions to form a reaction mixture comprising an alkylation product, wherein the surfactant has a solubility at room temperature of 0.5% or less in the olefin, the isoparaffin or aromatic compound, the sulfuric acid, and the alkylation product, wherein an amount of the surfactant is in a range of 0.010 to 0.25 wt % of an amount of the sulfuric acid, and wherein a molar feed ratio of liquid acid to olefin is in a range of 0.0051 to 1001 An embodiment of the invention is one, any or all of prior embodiments in this paragraph up through the second embodiment in this paragraph wherein the surfactant comprises a quaternary ammonium cationic salt, or a quaternary phosphonium cationic salt, or combinations thereof. An embodiment of the invention is one, any or all of prior embodiments in this paragraph up through the second embodiment in this paragraph further comprising separating the alkylation product from the reaction mixture. An embodiment of the invention is one, any or all of prior embodiments in this paragraph up through the second embodiment in this paragraph further comprising recycling at least a portion of the sulfuric acid, the surfactant, or both. An embodiment of the invention is one, any or all of prior embodiments in this paragraph up through the second embodiment in this paragraph wherein the olefin comprises a $C_2$-$C_{20}$ olefin. An embodiment of the invention is one, any or all of prior embodiments in this paragraph up through the second embodiment in this paragraph wherein the alkylation reaction conditions include one or more of a temperature of from 0° to 50° C., a pressure of from 100 kPa to 2100 kPa, or a liquid hourly space velocity of from 2.0 to 60.0 $hr^{-1}$.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for acid catalyzed alkylation comprising:
    reacting an olefin and an isoparaffin or an aromatic compound in the presence of a liquid acid catalyst and a surfactant in an alkylation reaction zone operating at alkylation reaction conditions to form a reaction mixture comprising an alkylation product, the reaction mixture comprising a Winsor Type III phase system, wherein the surfactant has a solubility at 25° C. of 0.5% or less in the olefin, the isoparaffin, the liquid acid catalyst, and the alkylation product.

2. The process of claim 1 wherein the surfactant comprises a quaternary ammonium cationic salt, or a quaternary phosphonium cationic salt, or combinations thereof.

3. The process of claim 2 wherein the quaternary ammonium cationic salt or a quaternary phosphonium cationic salt comprises a quaternary ammonium halide, a quaternary ammonium sulfate, a quaternary ammonium hydrogen sulfate, a quaternary ammonium nitrate, a quaternary ammonium carbonate, a quaternary ammonium bicarbonate, a quaternary phosphonium halide, a quaternary phosphonium sulfate, a quaternary phosphonium hydrogen sulfate, a quaternary phosphonium nitrate, a quaternary phosphonium carbonate, a quaternary phosphonium bicarbonate, or combinations thereof.

4. The process of claim 1 wherein the surfactant comprises dibutyl dioctyldecyl ammonium chloride, dimethyl dipentadecyl ammonium chloride, diethyl dipentadecyl ammonium chloride, dipropyl dipentadecyl ammonium chloride, dibutyl dipentadecyl ammonium chloride, dimethyl dihexadecyl ammonium chloride, diethyl dihexadecyl ammonium chloride, dipropyl dihexadecyl ammonium chloride, dibutyl dihexadecyl ammonium chloride, dimethyl dioctadecyl ammonium chloride, diethyl dioctadecyl ammonium chloride, dipropyl dioctadecyl ammonium chloride, dimethyl dinonadecyl ammonium chloride, diethyl dinonadecyl ammonium chloride, dipropyl dinonadecyl ammonium chloride, dibutyl dinonadecyl ammonium chloride, dimethyl diicosylecyl ammonium chloride, diethyl diicosyldecyl ammonium chloride, dipropyl diicosyldecyl ammonium chloride, dibutyl diicosyldecyl ammonium chloride, or combinations thereof.

5. The process of claim 1 further comprising:
    separating the alkylation product from the reaction mixture.

6. The process of claim 1 wherein an amount of the surfactant is in a range of 0.010 to 0.25 wt % of an amount of the liquid acid.

7. The process of claim 1 further comprising an additional surfactant or co-surfactant.

8. The process of claim 1 wherein a molar feed ratio of liquid acid to olefin is in a range of 0.005:1 to 100:1.

9. The process of claim 1 further comprising recycling at least a portion of the liquid acid, the surfactants, or both.

10. The process of claim 1 wherein the liquid acid comprises sulfuric acid, hydrofluoric acid, an acidic ionic liquid, or combinations thereof.

11. The process of claim 1 wherein the olefin comprises a $C_2$-$C_{20}$ olefin.

12. The process of claim 1 wherein the alkylation reaction conditions include at least one of: a temperature of from 0° to 50° C., a pressure of from 100 kPa to 2100 kPa, or a liquid hourly space velocity of from 2.0 to 60.0 $hr^{-1}$.

13. The process of claim 1 further comprising at least one of:
    sensing at least one parameter of the process and generating a signal or data from the sensing; or
    generating and transmitting a signal; or
    generating and transmitting data.

14. A process for sulfuric acid catalyzed alkylation comprising:
    reacting an olefin and an isoparaffin or aromatic compound in the presence of a sulfuric acid catalyst and a surfactant in an alkylation reaction zone operating at alkylation reaction conditions to form a reaction mixture comprising an alkylation product, the reaction mixture comprising a Winsor Type III phase system, wherein the surfactant has a solubility at room temperature of 0.5% or less in the olefin, the isoparaffin or aromatic compound, the sulfuric acid, and the alkylation product, wherein an amount of the surfactant is in a range of 0.010 to 0.25 wt % of an amount of the sulfuric acid, and wherein a molar feed ratio of liquid acid to olefin is in a range of 0.005:1 to 100:1.

15. The process of claim 14 wherein the surfactant comprises a quaternary ammonium cationic salt, or a quaternary phosphonium cationic salt, or combinations thereof.

16. The process of claim 14 further comprising:
    separating the alkylation product from the reaction mixture.

17. The process of claim 14 further comprising recycling at least a portion of the sulfuric acid, the surfactant, or both.

18. The process of claim 14 wherein the olefin comprises a $C_2$-$C_{20}$ olefin.

19. The process of claim 14 wherein the alkylation reaction conditions include one or more of: a temperature of from 0° to 50° C., a pressure of from 100 kPa to 2100 kPa, or a liquid hourly space velocity of from 2.0 to 60.0 $hr^{-1}$.

20. The process of claim 14, wherein the liquid acid comprises sulfuric acid, hydrofluoric acid, or combinations thereof.

\* \* \* \* \*